United States Patent
Clayton

(10) Patent No.: US 6,699,271 B2
(45) Date of Patent: Mar. 2, 2004

(54) THERAPEUTIC WRAPS

(76) Inventor: Neva A. Clayton, 104 Spruce La., Bridgewater, VA (US) 22812

(*) Notice: Subject to any disclaimer, the term of this patent is extended or adjusted under 35 U.S.C. 154(b) by 0 days.

(21) Appl. No.: 10/115,909

(22) Filed: Apr. 5, 2002

(65) Prior Publication Data

US 2002/0198580 A1 Dec. 26, 2002

Related U.S. Application Data

(63) Continuation-in-part of application No. 29/144,942, filed on Jul. 13, 2001, now abandoned, and a continuation-in-part of application No. 29/145,009, filed on Jul. 13, 2001, now abandoned.
(60) Provisional application No. 60/218,794, filed on Jul. 18, 2000, and provisional application No. 60/218,844, filed on Jul. 18, 2000.

(51) Int. Cl.$^7$ .................................................. A61F 7/00
(52) U.S. Cl. ........................................ 607/109; 607/96
(58) Field of Search ......................... 607/96, 108, 109, 607/110, 111, 112, 114; 602/2, 14; 165/46; D24/200, 206, 207, 208

(56) References Cited

U.S. PATENT DOCUMENTS

| | | |
|---|---|---|
| 103,026 A | 5/1870 | Dederick |
| D167,743 S | 9/1952 | Dorfman |
| 3,312,987 A | 4/1967 | Emery |
| 3,587,578 A | 6/1971 | Walker |
| 3,900,035 A | 8/1975 | Welch et al. |
| 4,516,564 A | 5/1985 | Koiso et al. |
| 4,517,972 A | 5/1985 | Finch, Jr. |
| 4,527,566 A | 7/1985 | Abare |
| 4,556,055 A | 12/1985 | Bonner, Jr. |
| 4,575,097 A | 3/1986 | Brannigan et al. |
| 4,586,506 A | 5/1986 | Nangle |
| 4,628,918 A | 12/1986 | Johnson, Jr. |
| 4,628,932 A | 12/1986 | Tampa |
| 4,669,476 A | 6/1987 | Gordon et al. |
| 4,671,267 A | 6/1987 | Stout |
| 4,706,658 A | 11/1987 | Cronin |
| D294,650 S | 3/1988 | De Beys |
| 4,802,667 A | 2/1989 | Altner |
| 4,805,620 A | 2/1989 | Meistrell |
| 4,860,748 A | 8/1989 | Chiurco et al. |
| 4,886,063 A | 12/1989 | Crews |
| 4,887,326 A | 12/1989 | O'Brien et al. |
| 5,005,374 A | 4/1991 | Spitler |
| D325,637 S | 4/1992 | O'Brien et al. |
| 5,176,134 A * | 1/1993 | Hudson ................. 607/114 |
| D336,958 S | 6/1993 | Pryor |
| D342,790 S | 12/1993 | Zona |
| 5,300,104 A | 4/1994 | Gaudreault et al. |
| 5,304,216 A * | 4/1994 | Wallace ................. 607/112 |
| D357,747 S | 4/1995 | Kelly |
| 5,507,793 A | 4/1996 | Hodges |
| D374,545 S | 10/1996 | Cionni |
| 5,571,155 A * | 11/1996 | Bastille ................. 607/114 |
| D380,051 S | 6/1997 | Davis et al. |
| 5,728,146 A | 3/1998 | Burkett et al. |
| 5,735,889 A | 4/1998 | Burkett et al. |
| D403,778 S | 1/1999 | Davis et al. |
| D407,824 S | 4/1999 | Davis et al. |
| D408,923 S | 4/1999 | Davis et al. |
| 5,890,487 A * | 4/1999 | Kimmel ................. 128/845 |

(List continued on next page.)

Primary Examiner—Roy D. Gibson
Assistant Examiner—Aaron Roane
(74) Attorney, Agent, or Firm—Mitchell B. Wasson, Esq.; Hoffman, Wasson & Gitler, PC

(57) ABSTRACT

A therapeutic wrap designed to be applied to various portions of an individual, such as the neck and shoulders. The wrap contains a plurality of narrow channels into which a filler material, such as Basmati rice, is provided. Various herbs such as chamomile or lavender are also provided within each of the channels to allow for aromatherapy.

5 Claims, 3 Drawing Sheets

U.S. PATENT DOCUMENTS

| | | |
|---|---|---|
| D412,750 S | 8/1999 | Davis et al. |
| D413,168 S | 8/1999 | Davis et al. |
| 5,948,010 A | 9/1999 | Adamec |
| D417,006 S | 11/1999 | Davis et al. |
| D417,283 S | 11/1999 | Davis et al. |
| 5,984,953 A | 11/1999 | Sabin et al. |
| D418,605 S | 1/2000 | Davis et al. |
| D418,606 S | 1/2000 | Davis et al. |
| 6,099,555 A | 8/2000 | Sabin |
| 6,123,717 A | 9/2000 | Davis et al. |
| 6,139,486 A * | 10/2000 | Matuszewski et al. ........ 600/15 |
| D433,757 S | 11/2000 | Jordan |
| D436,179 S * | 1/2001 | Small ........................ D24/206 |
| D453,223 S * | 1/2002 | Sherman .................... D24/206 |
| 6,537,308 B2 * | 3/2003 | Burkhart ..................... 607/109 |
| 2002/0042641 A1 * | 4/2002 | Johnson ...................... 607/114 |

\* cited by examiner

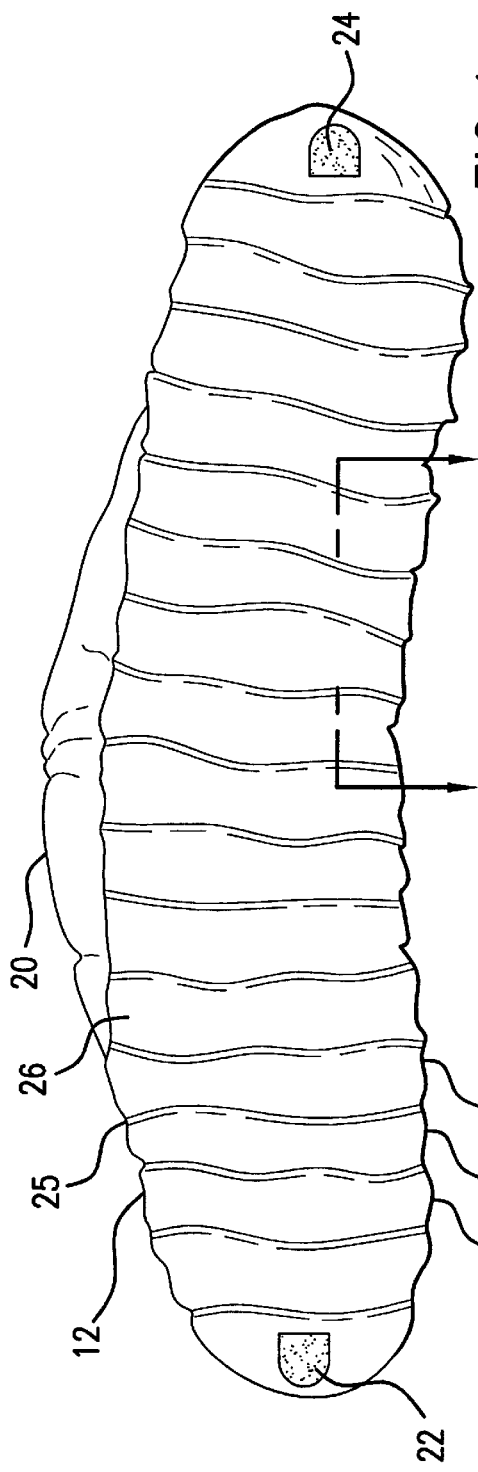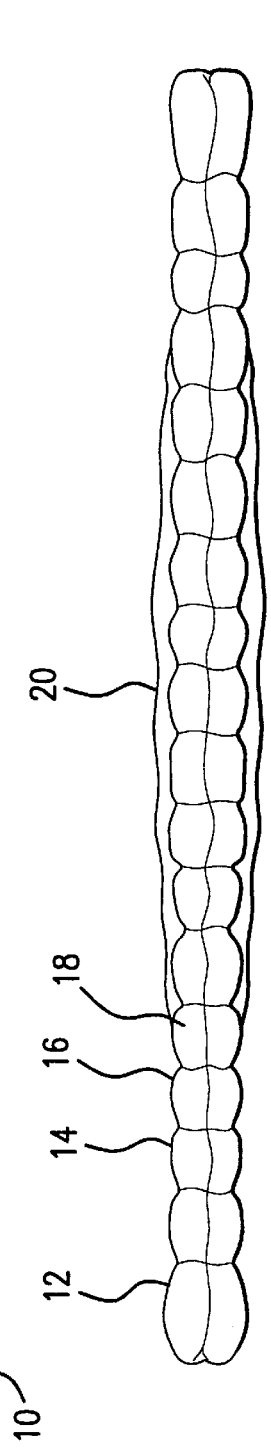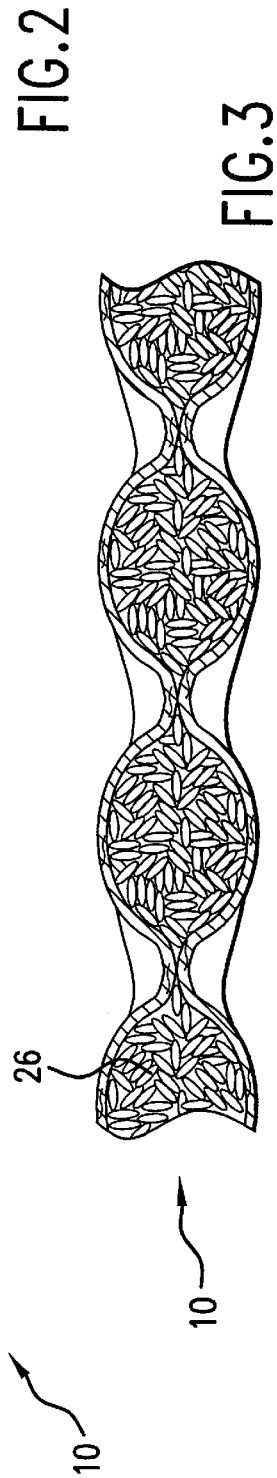

THERAPEUTIC WRAPS

The present continuation-in-part application claims the benefit of design applications 29/144,942, filed on July 13, 2001 now abandoned, as well as 29/145,009, filed on Jul. 13, 2001 now abandoned, as well as provisional application No. 60/218,794, filed Jul. 18, 2000 and No. 60/218,844, filed Jul. 18, 2000.

BACKGROUND OF THE INVENTION

1. Field of the Invention

The present invention is directed to therapeutic wraps for applying heat and cold to the human body.

2. Discussion of the Prior Art

It has been known for many years that the application of heat and cold to the body has not only many therapeutic benefits, but is also very relaxing to the individual to which it is administered. Generally speaking, if a user has recently been injured, it is preferable that cold and not heat be applied to the body to insure that swelling does not occur. After this initial period of time, heat can then be applied to the site of the injury, or for relaxation purposes.

Initially, heat was applied to the body of a user utilizing a hot water bottle. The bottle was usually manufactured from plastic and would be filled with hot water and then applied to the body of the user. However, as can be appreciated, the exterior of the hot water bottle would become moist and would be unpleasant to the user. Additionally, heat retention would only be for a short period of time. If cold were to be applied to a portion of the body, ice cubes would be inserted into a receptacle and then applied to the body of the individual. Similar to the hot water bottle, this was an inefficient and unpleasant way of administering cold to a portion of the body.

Subsequently, a number of devices were developed to improve the manner in which heat and cold are applied to the body. Some of these devices are embodied in various patents such as U.S. Pat. No. 4,887,326, issued to O'Brien et al, Design Pat. 342,790, issued to Zona and Design Pat. 433,757, issued to Jordan.

The patent to O'Brien et al describes a suboccipital pillow for applying hot and/or cold treatments to the neck and the suboccipital areas of the body. The pillow is generally of a crescent shape, one side of which is fitted with a lightly insulated pocket and the other side of which is fitted with a heavily insulated pocket into which crescent shape gel packs can be inserted after they are either heated or chilled. The pillow must be deep enough to be of sufficient depth to accommodate the length of the neck of the user in order to reach the posterior base of the skull or occiput. This particular design would be uncomfortable to be utilized for a long period of time and also would not cover the upper chest muscles, particularly the pectoralis minor muscles. These muscles, when tight, can overstretch the upper back muscles, thereby causing pain in the upper back.

The design patent to Zona illustrates a therapeutic neck wrap having a plurality of channels which it is assumed, are provided with a gel pack to which heat or cold are initially applied. However, the design of the Zona patent would prevent it from fitting sufficiently close to various portions of the neck and shoulder thereby preventing the most beneficial method of applying heat or cold to these portions of the body.

The design patent to Jordan illustrates a temperature packet presumably applied to the neck or shoulder of a user. However, the particular design of the Jordan temperature packet, similar to the suboccipital pillow issued to O'Brien et al would not provide enough surface area directly over the particular muscles that heat or cold should be applied.

In addition to the aforementioned U.S. patents which constitute a representative sample of the prior art, and do not cover a sufficient portion of the body to be effective in use, several additional prior art patents utilize a gel pack for heating and cooling. However, if these gel packs are overheated, they could place the user at risk if not properly insulated before use, or cooled to a more appropriate temperature. Additionally, if these gel packs provided in the prior art wraps are torn or punctured, the caustic chemicals provided therein could harm the user.

Several U.S. patents such as U.S. Pat. No. 5,984,953, issued to Sabin et al; U.S. Pat. No. 6,099,555, issued to Sabin and U.S. Pat. No. 5,948,010, issued to Adamec, have addressed this problem. For example, Sabin '555, describes a gelling cold pack, which could utilize starch, such as rice. Sabin et al '953 describes a self-regulating heat pack which also utilizes a starch, such as rice. The patent to Adamec illustrates a therapeutic heat application device employing a natural filler material which could be rice. However, these patents do not describe or illustrate a heat pack containing the appropriate filler material which both retains heat or cold for a reasonably long period of time, as well as being aromatic.

SUMMARY OF THE INVENTION

The present invention addresses the insufficiencies of the prior art by providing a therapeutic wrap which retains heat for a reasonably long period of time, as well as having the ability to be easily and comfortably placed over a number of areas of the body to which therapeutic heat would be applied very efficiently. The therapeutic wrap, according to the present invention can also be used to cool a particular portion of the body. The present invention is in the form of a shoulder wrap, as well as a neck wrap, designed to cover various portions of the user's body so that the various wraps are held close to the neck and shoulder muscles being treated with hot or cold therapies. Each of these wraps contain a plurality of narrow channels into which Basmati rice and herbs are inserted to act as a soothing agent applying heat and cold to the body. These narrow channels keep the rice from shifting, thereby holding it close to the neck and shoulder muscles being treated. When heated, the rice provided in the channels of both the shoulder and neck wraps would convey moist heat to the body for 25–45 minutes, depending upon the degree of original heat. This is safer therapy than using a heating pad as it gently decreases the heat as the pack cools, thereby reducing the risk of burns.

BRIEF DESCRIPTION OF THE DRAWINGS

These and other objects of the present invention will be described in more detail with respect to the following drawings in which:

FIG. 1 is a top view of a neck wrap of the present invention;

FIG. 2 is a side view of the neck wrap of the present invention;

FIG. 3 is a cross-sectional view through 1—1 of FIG. 1 of the neck wrap of the present invention;

DETAILED DESCRIPTION OF THE PRESENT INVENTION

Figure 4:
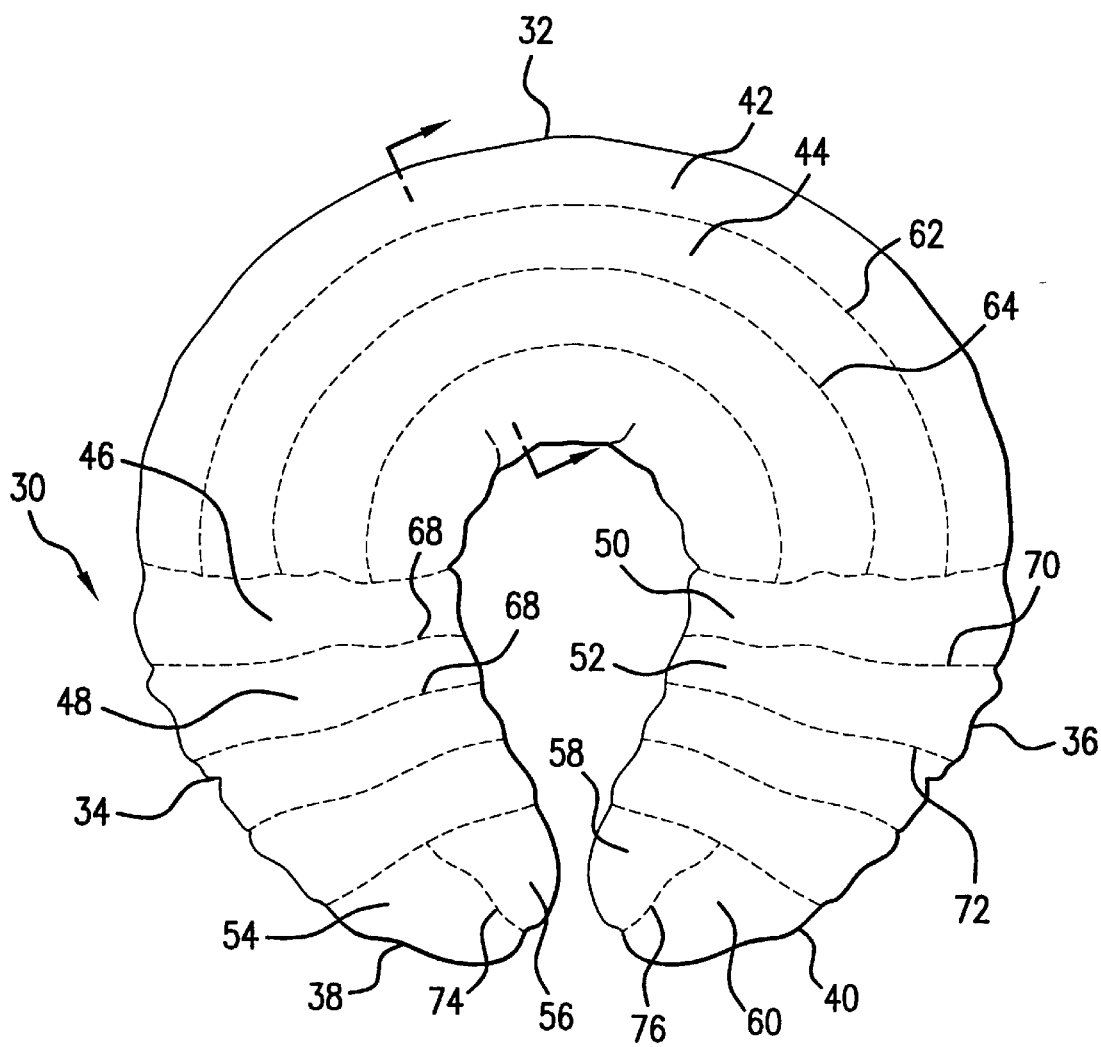
FIG. 4 is a top view of the shoulder wrap of the present invention.
Figure 5:
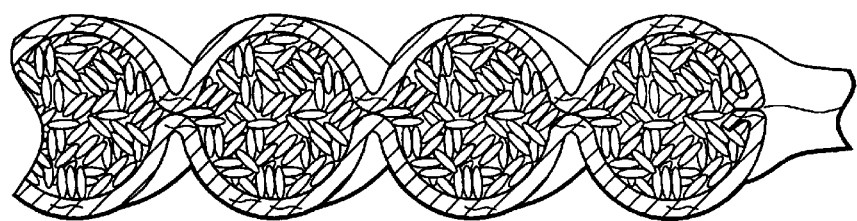
FIG. 5 is a cross-sectional view through 4—4 of FIG. 4 of the shoulder wrap of the present invention.

FIGS. 1, 2 and 3 illustrate the therapeutic neck wrap according to the present invention. This neck wrap 10 consists of a outer wrap material 12 formulated from cotton flannel or a similar material. The wrap includes a plurality of narrow channels 14, 16, 18, etc., into which a heat transferring material is inserted. Each channel is separated from its adjoining channel by stitching them closed such as shown by 25, 26. This configuration would allow complete separation of each channel from their adjoining channels and would allow for flexibility when applied to the surface of the body. Additionally, these narrow channels (approximately 1¼ inch to 1½ inch in width) would allow for better surface contact with the body. It is important to note that wider channels do not provide as much surface contact. The channels 14, 16, 18, etc., extend for the entire length of the neck wrap, which, in this embodiment, is approximately 22 inches long, measures approximately 6½ inches at its widest point, exhibits a thickness of approximately ¾ of an inch and weighs between one and two pounds. The neck wrap is provided with a extension 20 extending for approximately 50%–60% of the length of the neck wrap 10 and provided approximately in the middle thereof. This extension 20 gives the wrap more flexibility and allows it to bend quite easily, thereby conforming more closely to the curve at the base of the neck or along the curve of the occipital ridge (or posterior base of the skull), depending upon how the wrap is worn, with the horizontal extension 20 down or up. Although the measurements of the wrap of the present invention are included, it is noted that the exact length, width and weight of the neck wrap can be altered, depending upon the size of the user.

The neck wrap of the present invention is designed to completely encircle the neck of the user. Consequently, it is preferable that a fastening device should be employed for this purpose. Therefore, VELCRO-type fasteners 22 and 24 are utilized for this purpose. The VELCRO-type fasteners 22 and 24, along with the use of the narrow channels, would keep the filler material within the wrap from shifting and holding it close to the neck during treatment. It is noted that other types of fasteners could also be used. In this manner, heat is held against the posterior and lateral sides of the neck, where tension is most often experienced. It is also noted that the neck wrap can also be worn across the shoulders, particularly when the VELCRO-type fasteners 22 and 24 are not attached to one another.

As illustrated in FIG. 3, a filler material 26 is provided within each of the narrow channels for transferring heat to and from the body. It has been found that the use of Basmati rice is particularly good for conveying moist heat to the body for approximately 25–45 minutes, depending upon the degree of original heat. The use of Basmati rice with herbs, such as chamomile, lavender or other relaxing herbs would also allow for aromatherapy to play a part in relaxing the muscles. Basmati rice is a long grain rice which can absorb up to three times its weight in water and would retain moisture drawn from the air and then supply moist heat via the neck wrap to the treated areas. When worn with the extension 20 below the rest of the wrap, it can provide additional warmth or cold to the lower cervical vertebrae and upper trapezius and levator scapulae muscles. When the wrap 10 is worn with the extension 20 above the rest of the wrap, it would provide therapeutic heat or cold to the occipital region of the lower skull muscle and attachments thereto.

Figure 6:
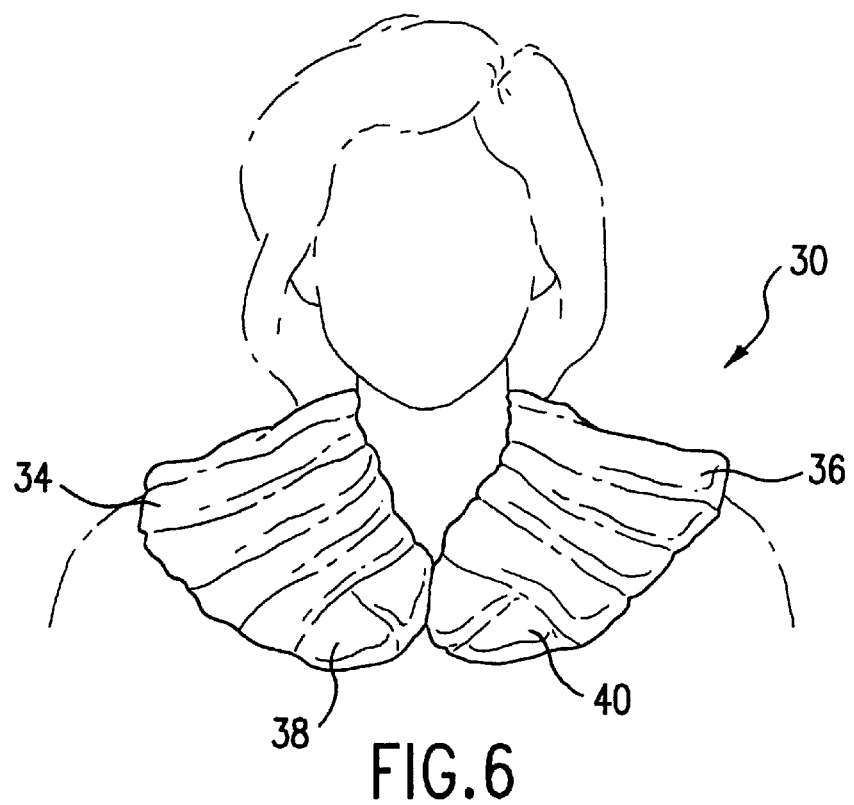
FIG. 6 is a front view of an individual utilizing the shoulder wrap of the present invention.
Figure 7:
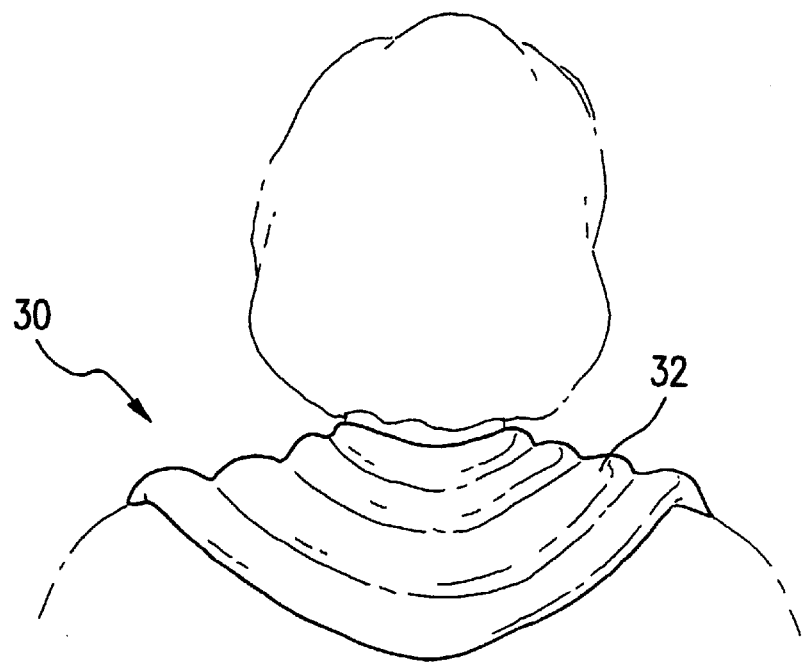
FIG. 7 is a back view of an individual utilizing the shoulder wrap of the present invention.

FIGS. 4, 5, 6 and 7 illustrate the therapeutic shoulder wrap according to the present invention. As shown in FIG. 4, the shoulder wrap 30 consists primarily of a crescent section 32, two winged sections 34, 36 and two end lobe sections 38, 40. The crescent section 32 consists of a plurality of narrow concentric channels 42, 44, etc., which form the back of the wrap. This crescent section allows more surface area of the wrap to be in contact with the muscles of the upper back, such as the upper trapezium, levator scapulae and rhomboids minor and part of the major. The length of the wrap over the shoulders and onto the upper chest allows it to apply heat or cold to the upper chest muscles such as the pectoralis minor, which, when tight, can adversely affect the upper back muscles by pulling the shoulders forward. The crescent section 32 is applied to the neck and shoulders as illustrated in FIG. 7. Wing portion 34 is provided with narrow channels 46, 48, etc., and wing portion 36 is provided with narrow channels 50, 52, etc. It is noted that the channels 46 and 50 are approximately perpendicular with the channels 42, 44, etc., of the crescent section 32. The remaining channels of the wing sections 34 and 36 are parallel to channels 46 and 50. The end lobe section 38 is provided with two channels 54 and 56. The end lobe section 40 is provided with two channels 58 and 60. It is noted that channels 54 and 56 are approximately perpendicular with the channels of the wing section 34 and channels 58 and 60 are approximately perpendicular with respect to the channels of the wing portion 36. As utilized, the wing portions 34 and 36, as well as the end portions 48 and 50, are shown in FIG. 6. The channels of the crescent portion 32, the wing portions 34, 36, as well as the end portions 38 and 40, are separated from one another by appropriate stitchings as shown by 62, 64, 66, 68, 70, 72, 74 and 76. The channels of both the crescent portion 32 and the wing portions 34, 36 are approximately 1¼ inch to 1½ inch in width. The shoulder wrap is about ¾ inch thick and weighs between 2 and 3 pounds. Similar to the neck wrap shown in FIGS. 1–3, each of the channels included in the shoulder wrap are filled by Basmati rice, as well as aromatic herbs such as lavender and chamomile.

It is noted that the weight of both the neck wrap and shoulder wrap is approximately 84%–84.5% Basmati rice. The aromatic herbs would constitute roughly 0.5%–1% of the wrap and the outer flannel covering would constitute approximately 15% of each of the wraps. However, it is noted that the exact composition of the wraps by weight are not crucial to the present invention. Furthermore, it is noted that the weight of the wraps is therapeutic, affording a comfortable pressure on the muscles without a sense of heaviness.

In use, the wraps are subjected to either heat by placing the wraps in a heated container, such as a conventional oven, crock pot or a microwave oven. Cold is applied to the wrap by placing it into a frigid environment, such as a refrigerator, freezer or icebox. After the wrap has been subjected to either heat or cold for an appropriate period of time, it is then applied to either the shoulder or the neck for a period of time such as between 20 and 45 minutes.

The description of the preferred embodiments of the present invention has been presented for purposes of illustration and description, but is not intended to be exhaustive or limit the invention in a precise form described. Obviously, many modification and variations will be apparent to practitioners skilled in the art. For example, the exact measurements of both the shoulder wrap and the neck wrap are not crucial to the present invention. The embodiments were chosen and described in order to best explain the principles of the invention and the practical application to enable others skilled in the art to understand the invention for various embodiments and with various modifications as are suited to the particular use contemplated.

What is claimed is:

1. A therapeutic wrap adapted to be placed on the shoulders of an individual, comprising:
    a cover;
    a crescent section including a plurality of curved concentric channel members provided with said cover; and
    filler material provided within said channel members for transferring heat to or from the body of the individual.

2. The therapeutic wrap in accordance with claim 1 further including first and second wing sections said first wing section non-contiguous with respect to said second wing section, each of said wing sections having a plurality of parallel wing channel members included within said cover, each of said wing channel members of said wing section being substantially perpendicular to said plurality of said curved concentric channel members and filled with filler material for transferring heat to and from the body of the individual, said first wing section abutting one end of said concentric channel members and said second wing section abutting the second end of said concentric channel members.

3. The therapeutic wrap in accordance with claim 2 further including a first end lobe section abutting said first wing section and a second end lobe section abutting said second wing section, said first and second end sections provided within said cover and each end lobe sections including a plurality of end channel members, said end channel members of said first end section being substantially perpendicular to said wing channel members of said first wing section and said end channel members of said second end section being substantially perpendicular to said wing channel members of said second wing section, each of said end channel members being filled with filler material for transferring heat to or from the body of the individual.

4. The therapeutic wrap in accordance with claim 3, wherein said filler material is Basmati rice.

5. The therapeutic wrap in accordance with claim 4 further including at least one aromatic herb provided in at least one of said end channel members, one of said wing channel members or one of said concentric channel members.

* * * * *